United States Patent
Ciolino

(10) Patent No.: US 11,554,104 B2
(45) Date of Patent: Jan. 17, 2023

(54) COMPOSITIONS FOR THE TREATMENT OF DRY EYE AND METHODS OF USE THEREOF

(71) Applicant: The Schepens Eye Research Institute, Inc., Boston, MA (US)

(72) Inventor: Joseph B. Ciolino, Boston, MA (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 0 days.

(21) Appl. No.: 16/639,945

(22) PCT Filed: Aug. 20, 2018

(86) PCT No.: PCT/US2018/000346
§ 371 (c)(1),
(2) Date: Feb. 18, 2020

(87) PCT Pub. No.: WO2019/036050
PCT Pub. Date: Feb. 21, 2019

(65) Prior Publication Data
US 2020/0246301 A1 Aug. 6, 2020

Related U.S. Application Data

(60) Provisional application No. 62/547,132, filed on Aug. 18, 2017.

(51) Int. Cl.
| | | |
|---|---|---|
| *A61K 31/26* | (2006.01) | |
| *A61K 9/00* | (2006.01) | |
| *A61K 9/48* | (2006.01) | |
| *A61K 36/31* | (2006.01) | |
| *A61K 47/10* | (2017.01) | |

(52) U.S. Cl.
CPC ............ *A61K 31/26* (2013.01); *A61K 9/0056* (2013.01); *A61K 9/4816* (2013.01); *A61K 36/31* (2013.01); *A61K 47/10* (2013.01)

(58) Field of Classification Search
None
See application file for complete search history.

(56) References Cited

U.S. PATENT DOCUMENTS

| | | |
|---|---|---|
| 3,429,426 A | 2/1969 | Weller et al. |
| 3,743,084 A | 7/1973 | Douglas |
| 4,840,797 A | 6/1989 | Boursier |
| 5,399,354 A | 3/1995 | Ells et al. |
| 5,616,340 A | 4/1997 | Ells et al. |
| 5,695,063 A | 12/1997 | Roulin et al. |
| 5,911,325 A | 6/1999 | Breitler |
| 6,219,997 B1 | 4/2001 | Friberg et al. |
| D444,379 S | 7/2001 | Assargren et al. |
| D455,344 S | 4/2002 | Assargren et al. |
| D455,953 S | 4/2002 | Assargren et al. |
| 2003/0170180 A1 | 9/2003 | Bahary |
| 2004/0031718 A1 | 2/2004 | Peng et al. |
| 2005/0031768 A1 | 2/2005 | Sakai et al. |
| 2009/0105313 A1 | 4/2009 | Yoshida et al. |
| 2011/0245213 A1 | 10/2011 | O'Kennedy et al. |
| 2013/0222406 A1* | 8/2013 | Wolfe ............... H04L 67/02 345/582 |
| 2014/0322366 A1 | 10/2014 | Rhyu et al. |
| 2016/0051443 A1 | 2/2016 | Depla |
| 2016/0081922 A1 | 3/2016 | Cho et al. |
| 2017/0071875 A1* | 3/2017 | Belmonte Mart Nez ............ A61K 31/7105 |

FOREIGN PATENT DOCUMENTS

| | | |
|---|---|---|
| CN | 105384671 | 3/2016 |
| JP | H09-065853 | 3/1997 |
| WO | WO 2012/074922 | 6/2012 |

OTHER PUBLICATIONS

International Preliminary Report on Patentability in International Appln. No. PCT/US2018/000346, dated Feb. 18, 2020, 7 pages.
International Search Report and Written Opinion in International Appln. No. PCT/US2018/000346, dated Jan. 9, 2019, 16 pages.
Senchyna & Wax, "Quantitative assessment of tear production: A review of methods and utility in dry eye drug discovery," J. Ocul. Biol. Dis. Infor., Mar. 2008, 1(1): 1-6.
EP Extended European Search Report in European Appln. No. 18846553.8, dated Mar. 5, 2021, 9 pages.
GNPD Database Accession No. 177571, "Congest-X Congestion Relief," Nov. 22, 2002, 2 pages.
Ratanasiriwat et al., "Properties of encapsulated wasabi flavour and its application in canned food," International Journal of Food Science and Technology, 2013, 48(4):749-757.
SoraNews24.com [online], "5 amazing health and beauty benefits of eating wasabi," SoraNews24—Japan News, Dec. 4, 2014, retrieved on Feb. 23, 2021, retrieved from URL <https://soranews24.com/2014/12/04/5-amazing-health-and-beauty-benefits-of-eating-wasabi/>, 4 pages.
Wasabi.org [online], "Not all wasabi capsules are made equal," Jun. 13, 2017, retrieved on Feb. 23, 2021, retrieved from URL <https://wasabi.org/not-all-wasabi-capsules-are-equal/>, 8 pages.
Office Action in Japanese Appln. No. 2020-509091, dated May 31, 2022, 12 pages (with English translation).

\* cited by examiner

*Primary Examiner* — Jessica Worsham
(74) *Attorney, Agent, or Firm* — Fish & Richardson P.C.

(57) ABSTRACT

The disclosure relates to compositions containing allyl isothiocyanate and methods of use thereof for stimulating tearing in a subject to treat dry eye.

9 Claims, 1 Drawing Sheet

COMPOSITIONS FOR THE TREATMENT OF DRY EYE AND METHODS OF USE THEREOF

CLAIM OF PRIORITY

This application is a 371 U.S. National Phase Application of PCT/US2018/000346, filed on Aug. 20, 2018, which claims the benefit of U.S. Provisional Patent Application Ser. No. 62/547,132, filed on Aug. 18, 2017. The entire contents of the foregoing are hereby incorporated by reference.

TECHNICAL FIELD

The invention relates to compositions and methods for inducing tearing to treat dry eye. The compositions contain allyl isothiocyanate and stimulate tearing upon ingestion by a subject.

BACKGROUND

Dry eye disease affects millions of people worldwide, and is a common condition in the United States. Dry eye disease is caused when an individual's tears do not provide adequate lubrication for the eyes, which can lead to inflammation and a further reduction in tear coverage. The symptoms of dry eyes include ocular discomfort and sensitivity, and impaired vision that can harm life quality. The risk of developing dry eye disease increases with age, and, as a result, the need for dry eye treatments is large and growing.

Current treatments for dry eye include eye drops or artificial tear substitutes, ointments, gels, nutritional supplements, warm compresses, punctal plugs, medications, topical cyclosporine, and electrical stimulation devices. However, many of these treatments offer temporary or incomplete relief to dry eye, are difficult or arduous to administer, or are unpleasant to the recipient of the treatment. For example, some eye drops do not provide sustained relief because while they add moisture to the eyes, they do not mimic the complex composition of tears, and may actually wash away or dilute beneficial tear components. Accordingly, effective treatments for dry eye that are easy to administer and minimally invasive to lifestyle are desired.

SUMMARY

The present invention arises from the clinical discovery that, when administered orally to a human, a composition comprising allyl isothiocyanate in a hydrated state causes substantially more tear production, i.e., lacrimation, than the same composition in a dehydrated state. This result was surprising because both the hydrated and dehydrated compositions, when administered directly to the eye, provoke brisk tear production. Furthermore, the dehydrated composition contains a much higher concentration of allyl isothiocyanate than the corresponding hydrated composition. The disparity between oral and ocular administration indicated that an orally administered dose form or composition, which acts locally to promote an immediate increase in tear production, could provide a more convenient, discreet, and biologically preferable means to treat dry eye disease than prevailing therapies e.g., eye drops, which are typically applied directly to the eye.

The compositions and methods disclosed herein enable the stimulation of therapeutic tearing in a subject. In particular, the compositions and methods stimulate tearing that therapeutically alleviates symptoms of dry eye, reduces dry eye symptoms, or prevents dry eye symptoms. The compositions disclosed herein contain a therapeutically effective amount of allyl isothiocyanate, a compound found in wasabi and horseradish that causes tearing. A subject having dry eye symptoms orally administers a composition containing allyl isothiocyanate so as to stimulate reflex tearing, thereby alleviating dry eye symptoms. Alternatively, a subject anticipating the onset of dry eye symptoms orally administers a composition containing allyl isothiocyanate so as to stimulate reflex tearing, thereby preventing the onset of dry eye symptoms.

As described herein, once administered in the mouth, wasabi and/or horseradish produce pungent vapors that stimulate the production of tears when the wasabi and/or horseradish are in a hydrated state, such as in a hydrated mixture or paste, but not when the wasabi and/or horseradish are in a dry or powdered form. Dry wasabi and horseradish powder lacks pungency. The powder needs to be hydrated for about 10 to 15 minutes before it becomes pungent and able to stimulate tearing. The compositions disclosed herein are designed to stimulate therapeutic tearing after oral administration in the mouth consistently, discreetly, cost-effectively, and with minimal effort, while reducing unpleasant sensations caused by the pungent aroma and the texture of wasabi paste. Wasabi paste can be divided into individual servings for consumption, but it is difficult to store, protect against spoilage and dehydration, and deliver a measured dose from a paste (such as toothpaste, other ointments and gels). By contrast, hard wasabi candies are sold commercially and could presumably deliver a more measured dose. However, these candies lack the pungency necessary to consistently induce tearing. Was described herein, and without wishing to be bound by theory, it is believed that the lack of pungency in commercially-sold wasabi candies results from the wasabi not being in a hydrated state in these candies. In addition, wasabi paste has a strong and pungent flavor and aroma that can be unpleasant if consumed on its own without food, and especially if consumed repeatedly to stimulate tears. Wasabi paste on its own also has a texture that can be unpleasant. The compositions disclosed herein provide a measured dose of a hydrated wasabi paste or aqueous mixture, maintain the wasabi paste in a hydrated state and protect it from spoilage, and can include a flavoring agent that masks the pungent flavor and aroma of wasabi.

In some implementations, the compositions are composed of a core containing a wasabi paste that is encapsulated in a shell. In some implementations, the compositions are composed of a core containing a hydrated mixture of wasabi that is encapsulated in a shell. The wasabi paste or hydrated mixture in the core comprises allyl isothiocyanate and water. In some implementations, the compositions are composed of a core that comprises allyl isothiocyanate and water that is encapsulated in a shell. The allyl isothiocyanate can be isolated and/or purified from a substance that naturally contains allyl isothiocyanate, e.g., wasabi or horseradish. The compositions can be provided as a candy, lozenge, capsule, pill, or chewing gum to stimulate tearing and alleviate dry eye symptoms.

The shell encapsulating the composition core contains the core, maintains the hydration of the core, and protects the core and its components from spoilage or contamination. The shell also allows for consistent and metered dosing, such that about the same amount of composition core can be orally administered in each candy, lozenge, capsule, pill, or piece of chewing gum. In some cases, the shell prevents the core from spoiling, and/or increases the shelf life of the composition, e.g., by increasing the length of time the composition can be kept at room temperature while retaining the capability to induce tearing in a subject. In some implementations, the shell encapsulates the core to keep it hydrated, e.g., by preventing evaporative water loss from the core. In some implementations, the shell encapsulates the core to contain and preserve allyl isothiocyanate, which is a volatile organic compound and can be chemically reactive. The shell encapsulating the composition core can be resistant to water. In some implementations, the shell encapsulating the composition core is a water insoluble shell. In some implementations, the shell encapsulating the composition core can be hypromellose, such as a hypromellose capsule. Alternatively, the shell can be sugar based, such as a shell used to coat hard candies. In some implementations, two or more shells encapsulate the core of the composition. For example, a soft shell can surround and contain the core, and a water-resistant shell can cover the soft shell. In another example, a hypromellose shell can surround the core, and a sugar-based hard candy shell can cover the hypromellose shell.

One use of this invention includes the oral administration of allyl isothiucyanate-containing paste or hydrated mixture, e.g., a wasabi paste, that is encapsulated in a water-resistant shell. By encapsulating the hydrated paste or mixture in a water-resistant shell, one can maintain the hydrated paste or mixture in a state that keeps the pungency of the allyl isothiocyanate-containing paste or mixture, which can be released by biting or melting the shell within the mouth. Upon ingestion, the allyl isothiocyanate-containing paste or hydrated mixture, e.g., wasabi paste, induces reflex tearing, thereby alleviating dry eye symptoms and/or preventing dry eye symptoms.

The compositions disclosed herein can be stored at room temperature in food packaging, such as a dispenser typically used to dispense candies such as mints, or a blister pack, such as those packs typically used to hold gum.

In a first aspect, the invention provides a composition for stimulating tearing when orally administered by a subject that comprises a core containing water and an effective amount of allyl isothiocyanate for stimulating tearing, and a shell encapsulating the core.

In some implementations, the core comprises a wasabi paste hydrated with water.

In some implementations, the shell is water-resistant. In some implementations, the shell comprises hypromellose. In some implementations, the shell comprises one or more layers of a hard candy shell. In some implementations, the shell comprises one or more layers of a hard candy shell comprising sugar. In some implementations, the shell is encapsulated in a second shell that is a hard candy shell comprising sugar. In some implementations, a hypromellose shell is further encapsulated in a hard candy shell comprising sugar.

In some implementations, the core comprises a flavoring agent. In some implementations, the hard candy shell comprises a flavoring agent. In some implementations, the flavoring agent is menthol or a menthol-containing oil.

In some implementations, the core stimulates tearing that therapeutically treats one or more symptoms of dry eye in the subject. In some implementations, the core stimulates an increase in tear production by over 10 mm in the subject, as measured on a Schirmer's test, e.g., an increase of 10, 11, 12, 13, 14, 15, 16, 17, 18, 19, 20, 21, 22, 23, 24, 25, 26, 27, 28, 29, or 30 mm or more on a Schirmer's test.

In another aspect, the invention provides a method of manufacturing a composition for stimulating tearing when orally administered by a subject. The method includes the steps of: (a) providing a core comprising water and an effective amount of allyl isothiocyanate for stimulating tearing; and (b) encapsulating the core in a shell.

In some implementations, the core in the method of manufacturing comprises a wasabi paste hydrated with water. In some implementations, the shell comprises hypromellose. In some implementations, the shell comprises one or more layers of a hard candy shell. In some implementations, the shell comprises one or more layers of a hard candy shell comprising sugar. In some implementations, the method further comprises encapsulating the hypromellose shell in a hard candy shell comprising sugar. In some implementations, the method further comprises adding a flavoring agent to the core or shell.

In another aspect, the invention provides a method for treating dry eye in a subject in need thereof, the method comprising administering to the mouth of the subject an oral dose form comprising: a core comprising water and allyl isothiocyanate; and a shell, wherein the shell encapsulates the core; wherein the subject suffers from dry eye; and wherein administering the oral dose form increases production of tears in the subject.

In some implementations, the core in the method for treating dry eye comprises a wasabi paste hydrated with water. In some implementations, the shell comprises hypromellose. In some implementations, the shell comprises one or more layers of a hard candy shell. In some implementations, the shell comprises one or more layers of a hard candy shell comprising sugar. In some implementations, the method further comprises encapsulating the hypromellose shell in a hard candy shell comprising sugar. In some implementations, the method further comprises adding a flavoring agent to the core or shell.

In some implementations, administering the oral dose form to a subject to treat dry eye increases tear production by over 10 mm, as measured on a Schirmer's test. In some implementations, administering the oral dose form increases tear production by over 15 mm, as measured on a Schirmer's test. In some implementations, administering the oral dose form increases tear production by over 20 mm, as measured on a Schirmer's test.

In another aspect, the invention provides a blister pack comprising two or more blisters, wherein each blister contains a composition for stimulating tearing when orally administered by a subject, wherein the composition comprises a core comprising water and an effective amount of allyl isothiocyanate for stimulating tearing; and a shell encapsulating the core.

In some implementations, the core of the blister pack comprises a wasabi paste hydrated with water. In some implementations, the shell of the blister pack comprises hypromellose. In some implementations, shell comprises one or more layers of a hard candy shell comprising sugar. In some implementations, the core of the blister pack stimulates tearing that therapeutically treats one or more symptoms of dry eye in the subject.

In another aspect, the invention provides a method for treating dry eye in a subject in need thereof, the method comprising administering to the mouth of the subject an oral dose form comprising: a core comprising water and allyl isothiocyanate; and a shell, wherein the shell encapsulates the core; wherein the subject suffers from dry eye; and wherein the administering increases production of tears in the subject. Any of the compositions described herein can be administered to the mouth of the subject as an oral dose form to treat dry eye in the subject in need thereof.

As used herein, "dry eyes" or "dry eye disease" means a condition wherein the tears produced by a subject's eyes do not provide adequate lubrication for the eyes, leading to symptoms whereby the subject experiences ocular discomfort or pain. Dry eyes can result from insufficient tear coverage on the surface of the eye that can hinder gas exchange, impair nutrient transport for the eyes, and create a poor refractive surface for vision. Poor eye lubrication can occur from decreased aqueous tear production by the lacrimal glands, excessive tear evaporation caused by dysfunction of the Meibomian glands, or from an imbalance in the makeup of tears (poor quality tears). Dry eye disease can be progressive, such that low volumes of tears can lead to inflammation of the ocular surface, which can induce apoptosis of surface cells, which in turn can prevent proper distribution of tear film on the ocular surface. The symptoms of dry eye include a stinging, burning or scratching sensation; mucus in or around eyes; eye redness; a gritty or sandy sensation; blurred vision; eye fatigue; sensitivity to light; difficulty wearing contact lenses; and difficulty seeing while driving. Dry eye can be diagnosed during a comprehensive eye exam, and by measuring tear production (the volume of tears) using the Schirmer's test. In a Schirmer's test, blotting strips of filter paper are placed under the lower eyelids for several minutes (e.g., the eyes are closed for 5 minutes) to measure the production of tears. The filter paper strip is removed, and the amount of strip soaked by tears is measured. Typically, a young person normally moistens 15 mm of each paper strip in 5 minutes, while an older individual may moisten about 10 mm in 5 minutes. The quality of tears may also be determined by applying eye drops containing dyes to assess the surface conditions of the eyes and measure the rate at which tears evaporate.

As used herein "corneal neuropathic disease" refers to a disease cause by damage to the nerves of the cornea that presents with symptoms that can be very similar to those of dry eye disease. The eyes of a subject with corneal neuropathic disease are also susceptible insufficient tearing. Treatments that increase tearing can reduce the symptoms of corneal neuropathic disease.

As used herein, "wasabi" means a product of a plant of the *Brassicaceae* family, of the genus *Wasabia*, e.g., *Wasabia japonica* or *W tenui*, that is typically used as a food condiment with a strong pungency that produces vapors that stimulate nasal passages and induce tearing. Wasabi contains allyl isothiocyanate (also known as 3-isothiocyanatoprop-1, molecular formula $C_4H_5NS$), which is responsible for inducing tearing. Wasabi is typically sold as a dry power that takes on flavor and pungency when water is added to become a paste. Wasabi powder lacks taste or potency, even when hydrated with the mouth's natural saliva. When water is added to wasabi powder to form a paste, the paste develops flavor and pungency after about 10 to 15 minutes. Wasabi is also sold as a paste in tubes or packets. Horseradish, radish, and mustard (e.g., hot mustard) also contain allyl isothiocyanate and are capable of causing a nasal sensation that induces tearing, and can therefore be substituted for wasabi in the compositions and formulations disclosed herein. For the purposes of this disclosure, "wasabi paste" can include preparations made from fresh wasabi rhizomes, or wasabi powder that is mixed with water to make a paste.

Allyl isothiocyanate (IUPAC name: 3-Isothiocyanato-1-propene, CAS 57-06-7) is a volatile organic compound with the formula $C_4H_5NS$ that is responsible for the pungent taste of wasabi, mustard, horseradish and radish. Allyl isothiocyanate is a lachrymator, capable of inducing tearing. The pungency and lachrymatory effects of allyl isothiocyanate are mediated through the TRPA1 and TRPV1 ion channels. Allyl isothiocyanate is slightly soluble in water, but well soluble in organic solvents.

As used herein with reference to a dose form, the composition can be composed of one or more materials in a particular physical arrangement, and said materials can be of more than one physical phase, e.g., solid, semisolid, and/or liquid. Thus, for example, as used herein, the composition can include an oral dose form comprising a liquid, semi-solid, and/or solid core and a solid shell, wherein the shell encapsulates the core; and such composition can optionally include other components, which are optionally placed in a particular physical arrangement.

As used herein, "shell" or "coating" refers to a layer of a material or substance applied to the surface of a composition, thereby surrounding the entire surface of the composition. The shell can be applied evenly over the surface of the composition, such that the shell is the same thickness at any given place on the composition. Alternatively, the shell can be applied unevenly over the surface of the composition, such that the thickness of the shell varies. The shell can be water resistant or water impermeable. The shell can be hydrophobic, or, alternatively, hydrophilic. The shell can be composed largely of a sugar, such as hard candy shell made of a mixture of sugar and corn syrup.

As used herein, "stimulate" or "induce" means to cause the onset of an event. For the purposes of the compositions and methods disclosed herein, "stimulate" or "induce" means to cause the onset of tearing, e.g., tearing in the eyes of a subject. In particular, the compositions described herein stimulate or induce tearing in a subject who has orally administered one of the compositions.

As used herein, "tearing" means the production of tears for lubrication and coverage of the eyes. A tear film has at least three layers or components, including a mucin layer, an aqueous layer, and a lipid layer. In some cases, "tearing" means an increased production of one or more of mucin, aqueous tears, and/or lipids. In some cases, "tearing" means the increased production of mucin and/or aqueous tears. In some cases, the compositions and methods described herein increase tearing in a subject.

As used herein, "basal tearing" refers to the tears that keep the eye, including the cornea, lubricated and nourished. Basal tears contain several components, including water, mucin, lipids, lysozymes, lactoferrin, lipocalin, lacritin, immunoglobulins, glucose, urca, sodium, potassium, and antioxidants. In some cases, the compositions and methods described herein increase basal tearing in a subject.

As used herein, "reflex tearing" refers to the automatic or reflexive tearing by the eyes of a subject that occurs in response to the subject's exposure to an environmental cue, compound or substance that induces tearing, e.g., a pungent or lachrymatory compound. In some cases, the compositions and methods described herein increase reflex tearing in a subject.

As used herein, "subject" refers to an animal. A subject can include a mammalian subject, such as, for example, a human, monkey, dog, cat, horse, cow, sheep, goat, llama, rabbit, or mouse. A subject can be a patient, e.g., a patient suffering from dry eye.

As used herein, administration to the mouth of a subject can include administration to any portion of the oral or buccal cavity or the oropharynx, the lips, gums, or tongue of the subject.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

The compositions and methods described herein provide oral allyl isothiocyanate formulations that stimulate tearing in a subject upon ingestion to prevent or therapeutically treat and/or reduce the severity of symptoms caused by insufficient eye lubrication from tears, such as ocular discomfort or impaired vision. Such allyl isothiocyanate formulations can be used to prevent or therapeutically treat and/or reduce the severity of symptoms of dry eye. For example, a subject having dry eye symptoms orally ingests a composition containing allyl isothiocyanate so as to stimulate tearing, thereby alleviating dry eye symptoms. Alternatively, a subject anticipating the onset of dry eye symptoms orally ingests a composition containing allyl isothiocyanate so as to stimulate tearing, thereby preventing the onset of dry eye symptoms. The allyl isothiocyanate formulations can be also used to prevent or therapeutically treat and/or reduce the severity of symptoms of corneal neuropathic disease.

Compositions for Inducing Therapeutic Tearing

The compositions described herein can be used to induce tearing in a subject, and more specifically, to alleviate the symptoms of dry eye or corneal neuropathic disease. The compositions have a core comprising the active ingredient, and at least one layer of a shell that encapsulates the core and maintains hydration and contains volatile compounds.

Core

Figure 1:
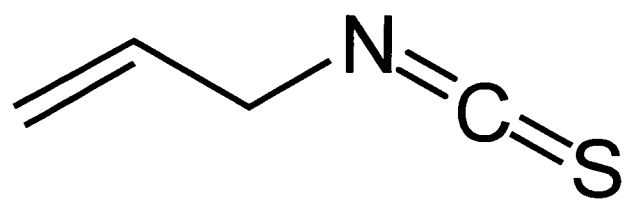
FIG. 1 is a schematic depicting the structure of allyl isothiocyanate.

The compositions are composed of a core comprising water and a sufficient amount of a substance comprising allyl isothiocyanate having pungent and lachrymatory characteristics that induce tearing in a subject who has chewed or ingested the substance, but do not physically harm the subject. The core can comprise a substance that contains allyl isothiocyanate, such as a preparation of wasabi, horseradish, radish, mustard, or the like. FIG. 1 depicts the structure of allyl isothiocyanate. In some implementations, the core comprises one or more of wasabi, horseradish, radish, or mustard.

Wasabi, horseradish, radish, and mustard can be prepared from a plant (e.g., from a rhizome), or purchased commercially as packets of dry powder, or as tubes of hydrated mixtures where a dry powder has been mixed with water or an oil to form a paste. As described herein, the wasabi powder has by itself little flavor or pungency, but must be hydrated for approximately 10 to 15 minutes before it develops pungent characteristics. The compositions described herein are based in part on the observation that wasabi powder that is hydrated with water has a pungency and lachrymatory effect that is greater than that of wasabi that is not hydrated or is combined with oil, and is therefore much more effective at inducing tearing upon oral ingestion. Thus, the compositions and methods described herein have been developed to encapsulate a hydrated mixture of wasabi (or horseradish, mustard, or radish) that can be stored stably until the wasabi composition is consumed, for example, until it is necessary to consume the composition to alleviate dry eye symptoms or corneal neuropathic pain. In some implementations, the composition is a pharmaceutically acceptable formulation of a hydrated mixture of wasabi that stimulates therapeutic tearing when consumed by a subject.

The compositions described herein also allow for the consistent administration of an effective amount of hydrated wasabi, e.g., an amount that is sufficient to induce therapeutic tearing consistently. The cores of the compositions described herein contain an effective amount of wasabi paste or a hydrated mixture containing allyl isothiocyanate. As used herein, the phrase "effective amount" refers to an amount sufficient to stimulate tearing and reduce the symptoms of dry eye or corneal neuropathic pain. For example, the core of a composition can contain an effective amount of wasabi paste sufficient to induce tearing in a subject. By contrast, it is difficult to repeatedly ingest an effective amount of wasabi paste that has been commercially purchased in a tube without measuring a precise amount of paste from the tube each time a dose is consumed.

In some implementations, the compositions are composed of a core containing a wasabi paste or hydrated mixture that is made of a hydrated wasabi, e.g., wasabi powder that is mixed with water. In some implementations, the core is a horseradish paste or hydrated mixture made of a horseradish powder that is mixed with water, a mustard paste or hydrated mixture made of a mustard powder that is mixed with water, or a combination of two or more of a wasabi paste, a horseradish paste, and/or a mustard paste mixed with water. In some implementations, a commercial wasabi powder is mixed with water according to the instructions provided by the manufacturer. However, the core of the composition can comprise wasabi paste made using any ratio of commercially-purchased wasabi powder and water, as long as the paste induces tearing when ingested. In some implementations, the core is made from a commercially purchased pre-mixed wasabi paste that contains wasabi hydrated in water.

In some implementations, water is added to wasabi powder to produce a hydrated paste having a moisture content between 10 and 80% by weight. Here, moisture content refers to the weight of the water expressed as a percentage of the total weight of the paste. In some implementations, the wasabi paste has a moisture content of between 10 and 20%, between 15 and 25%, between 20 and 30%, between 25 and 35%, between 30 and 40%, between 35 and 45%, between 40 and 50%, between 45 and 55%, between 50 and 60%, between 55 and 65%, between 60 and 70%, between 65 and 75%, or between 70 and 80%. In some implementations, water is added to wasabi powder in the amount suggested by instructions provided by the wasabi powder manufacturer. In some implementations, water is added to wasabi powder in a ratio of, e.g., about 1:2 (w/w, powder to water) up to 5:3, e.g., 1:2, 2:3, 3:5, 5:7, 1:1, 7:5, of 5:3. In some implementations, 2.5 g of wasabi powder is mixed with 3.5 g of water to produce a hydrated paste.

The core can also be made of a mixture comprising allyl isothiocyanate that has been synthesized, or has been isolated from a natural source of allyl isothiocyanate, e.g., wasabi or horseradish. In some implementations, the allyl isothiocyanate has been purified from a natural source. Various processes have been described for synthesizing, isolating, and/or purifying allyl isothiocyanate, for example, as described in U.S. 2005/0031768, and CN 105384671, each of which is incorporated herein by reference in its entirety. In some implementations, allyl isothiocyanate is produced by the reaction of allyl chloride and potassium thiocyanate, or by dry distillation of the seeds of black mustard (*Brassica nigra*) or brown Indian mustard (*Brassica juncea*), or from the rhizome of wasabi or horseradish (genus *Armoracia*). In some implementations, when the core is prepared by hydrating a wasabi or other powder, the core is encapsulated by the shell within 10-20 minutes of hydration to preserve the potency of the core.

In some implementations, and effective amount of wasabi in the core of a composition is 50 mg to 2,000 mg of wasabi paste made from wasabi powder and water. In some implementations, the effective amount is 50 mg to 250 mg of wasabi paste made from wasabi powder and water. In some implementations, the effective amount is 100 mg to 300 mg of wasabi paste made from wasabi powder and water. In some implementations, the effective amount is 250 mg to 450 mg of wasabi paste made from wasabi powder and water. In some implementations, the effective amount is 400 mg to 600 mg of wasabi paste made from wasabi powder and water. In some implementations, the effective amount is 550 mg to 750 mg of wasabi paste made from wasabi powder and water. In some implementations, the effective amount is 700 mg to 900 mg of wasabi paste made from wasabi powder and water. In some implementations, the effective amount is 850 mg to 1050 mg of wasabi paste made from wasabi powder and water. In some implementations, the effective amount is 1000 mg to 1200 mg of wasabi paste made from wasabi powder and water. In some implementations, the effective amount is 1150 mg to 1350 mg of wasabi paste made from wasabi powder and water. In some implementations, the effective amount is 1300 mg to 1500 mg of wasabi paste made from wasabi powder and water. In some implementations, the effective amount is 1450 mg to 1650 mg of wasabi paste made from wasabi powder and water. In some implementations, the effective amount is 1600 mg to 1800 mg of wasabi paste made from wasabi powder and water. In some implementations, the effective amount is 1750 mg to 2000 mg of wasabi paste made from wasabi powder and water. In some implementations, the effective amount is 200 mg to 800 mg of wasabi paste made from wasabi powder and water. In some implementations, the effective amount is 200 mg to 800 mg of a wasabi paste or hydrated mixture.

In some implementations, the content of allyl isothiocyanate in the composition may be, but is not limited to, between 0.0001 to about 5% by weight, based, on the total weight of the final composition. In some implementations, the content of allyl isothiocyanate in the wasabi paste may be, but is not limited to, between 0.0001 to about 5% by weight, based, on the total weight of the final wasabi paste.

In some implementations, the compositions disclosed herein are formulated to include one or more food preservatives known in the art. A food preservative can be added to the wasabi paste and/or the shell to help prevent the growth of microorganisms such as bacteria and reduce the risk of spoilage during storage.

In some implementations, the compositions disclosed herein can be formulated with one or more flavoring agents. Various flavoring agents are well known in the art, and have been used extensively by the food and pharmaceutical industries to add flavor to ingestible products or to mask unpleasant flavors. One of skill in the art would understand that any flavoring agent or combination of flavoring agents can be added to the compositions described herein. For example, flavoring agents that add flavors such as, but not limited to, mint, peppermint, spearmint, vanilla, cinnamon, chocolate, and fruit flavors, such as cherry, strawberry, blueberry, banana, or orange, can be added to the compositions. One or more flavoring agent can be added to the core of a composition, to the shell of a composition, or to the core and to shell of a composition. In some implementations, menthol or a menthol-containing oil (e.g., oil of peppermint or corn mint) is provided in the core as a flavoring agent; the menthol confers other desirable properties, including a cooling or anesthetic effect in the mouth and oropharynx, and additional stimulation of tearing in the eyes. A flavoring agent can include a sweetener, e.g., glucose, fructose, aspartame, or Stevia extract.

Encapsulation

The core formulations of the compositions are encapsulated so as to contain the core, maintain the hydration of the core, and protect it from contamination until it is ready to be consumed by a subject to induce tearing. In some implementations, the core is encapsulated in at least one shell layer so that the core can be stably stored in a hydrated state that maintains the lachrymatory effects of the core. Allyl isothiocyanate is a volatile organic compound. In some implementations, the core is encapsulated in at least one shell layer to contain allyl isothiocyanate. The core can also be encapsulated in a shell to reduce the possibility of spoilage and increase the storage life of the composition. The shell can also be used to enhance the experience of consuming the composition for the subject, for example, by changing the flavor of the composition so as to reduce or mask the pungent flavor of wasabi, and/or by masking the aroma of the wasabi.

In some implementations, the core can be coated in a shell that can be broken by biting or chewing, thereby allowing the rapid exposure of the core to the mouth of a subject at once, so as to induce tearing rapidly. In some implementations, the shell dissolves quickly in the mouth of a subject, e.g., in response to saliva, thereby allowing the rapid exposure of the core in the mouth at once, so as to induce tearing rapidly. In other implementations, the shell dissolves slowly in the mouth of a subject, e.g., in response to saliva, exposing only a portion of the core to the mouth over time, thereby stimulating a milder tearing effect over a longer period of time.

In some implementations, the shell is made of a hydrophobic material or compound. In some implementations, the shell is water-resistant. In some implementations, the shell is water-impermeable. In some implementations, the shell is made of a hydrophilic material or compound. In some implementations, the shell is not water resistant.

In some implementations, the shell is made of hypromellose, or a similar substance. Hypromellose is also known in the art as hydroxypropylmethylcellulose (HPMC), and is produced by several chemical companies under different trade names. The type of hypromellose used to produce the shell for the compositions described herein includes all types of hypromellose recognized in the art as being pharmaceutically acceptable. In some implementations, the core of a composition disclosed herein can be placed into a hypromellose capsule, e.g., a pre-fabricated hypromellose capsule that can be purchased commercially. For example, the core of a composition can be placed into a hypromellose capsule, such as a hypromellose capsule produced by CAPSUL- GEL®. Thus, in some implementations, a core containing allyl isothiocyanate, e.g., a wasabi paste or hydrated mixture, can be placed into a hypromellose capsule for consumption by a subject.

The compositions described herein can be stored at a variety of temperatures. For example, the compositions can be stored under refrigeration, e.g., at about 4° C. In some implementations, the compositions can be stored at room temperature, e.g., 20° C. to 25° C. In some implementations, the composition can be stored at room temperature for one or more days, e.g., for 1 to 365 days or more. In some implementations, the compositions can be stored at room temperature for 1 to 365 days, 15 to 340 days, 30 to 325 days, 45 to 305 days, 60 to 290 days, 75 to 275 days, 100 to 250 days, 115 to 235 days, 130 to 210 days, 145 to 195 days, or 160 to 180 days. In some implementations, the compositions can be stored for 2 weeks, 4 weeks, 6 weeks, 8 weeks, 10 weeks, 12 weeks, 14 weeks, 16 weeks, 18 weeks, 20 weeks, 22 weeks, 24 weeks, 26 weeks, 28 weeks, 30 weeks, 32 weeks, 34 weeks, 36 weeks, 38 weeks, 40 weeks, 42 weeks, 44 weeks, 46 weeks, 48 weeks, 50 weeks, 52 weeks, 54 weeks, 56 weeks, or more. In some implementations, the compositions can be stored for 6 months, 1 year, 2 years, 3 years, 4 years, or 5 years, or more.

In some implementations, the shell is made of a sugar-based coating. For example, the shell can be a hard candy shell, coating, glaze, or shellac that is, e.g., made out of sugar and corn syrup. In some implementations, the sugar-based shell is water resistant. Various processes for applying hard-candy shells to products, such as candies and pharmaceutical products, are known in the art and can be used to coat the compositions disclosed herein with a hard candy shell. A few examples for applying hard-candy shells to products are described in U.S. Pat. Nos. 4,840,797, 5,399,354, and 5,616,340, herein incorporated by reference in their entirety. In some implementations, a core containing allyl isothiocyanate, such as a core containing wasabi paste, can be dipped into a melted mixture of one-part water, two parts sugar, and 0.5 parts corn syrup, and then set to cool, thereby allowing the coating to harden into a hard candy shell. In some implementations, the composition consists of a core formulation containing an aqueous wasabi mixture or wasabi paste surrounded by a water resistant or water impermeable candy coating.

Figure 2:
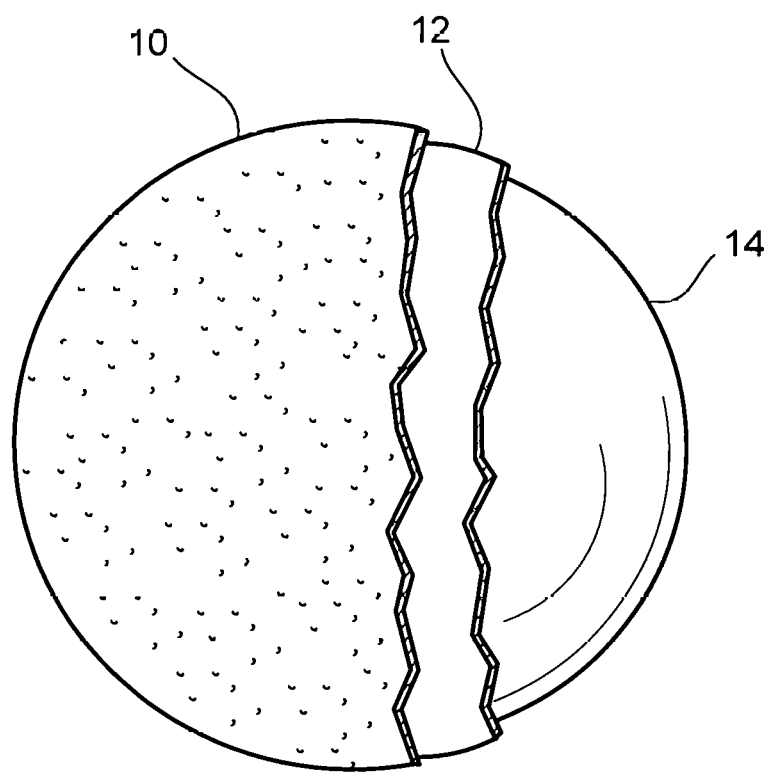
FIG. 2 is a schematic depicting a composition as described herein.

In some cases, it is advantageous to encapsulate the cores of the compositions disclosed herein with two or more shells. For example, two or more shells can more stably contain the core and keep it hydrated during storage. The use of two or more shells can also aid in the process of making the compositions, e.g., a first shell, such as shell made of hypromellose, can be applied to contain the core and keep it hydrated until a second hard candy shell can be applied. In some implementations, the compositions disclosed herein can include a core coated with a hypromellose shell and a water-resistant shell. In some implementations, the compositions disclosed herein can include a core coated with a hypromellose shell and a hard candy shell. FIG. 2 depicts a schematic of the layers of a composition described herein, containing a core 14 encapsulated by a hypromellose shell 12 and a hard candy shell 10. In some implementations, the core is coated directly with a hypromellose shell, and a hard candy shell is overlaid on top of the hypromellose shell. In some implementations, the core is coated directly by a hard candy shell, and a hypromellose shell in overlaid on top of the hard candy shell. In some implementations, a core containing wasabi paste or a hydrated wasabi mixture is placed in a hypromellose capsule, and a hard candy shell is overlaid on top of the hypromellose capsule.

In some implementations, the compositions disclosed herein can be produced into a chewable candy, a lozenge, a pill, or a capsule for consumption by a subject. For example, biting or chewing the candy or sucking on the lozenge exposes the mouth of the subject to the core mixture, thereby inducing tearing in the subject.

Storage

In some implementations, the compositions disclosed herein can be stored and sold, for example, in blister packs, dispensers, or similar packaging that allow a subject to select and consume individual units or doses of the compositions. For example, the compositions can be in the form of candies or lozenges that are stored in blister packs similar to those blister packs used in the commercial sale of chewing gum. The blister packs, dispensers, and packaging can keep the compositions dry so as to reduce the possibility of loss of potency, e.g., ability to simulate tearing, prevent melting or spoilage of the compositions, and increase the shelf-life of the compositions. Blister packs, dispensers and packaging suitable for the storage of the compositions disclosed herein have long been used by the food and pharmaceutical industries, and are well known in the art. For example, suitable blister packs, dispensers, or packaging are disclosed in U.S. Pat. Nos. 3,429,426, 3,743,084, 5,911,325, 5,695,063, 6,219,997, U.S. 2004/0031718, U.S. 2016/0051443, U.S. D444379, U.S. D455344, and U.S. D455953, which are herein incorporated by reference in their entirety.

Methods of Administering Compositions to Induce Tearing

The present disclosure provides a method for inducing tearing in a subject in need thereof, the method comprising administering to the mouth of the subject an oral dose form comprising: a core comprising water and allyl isothiocyanate; and a shell, wherein the shell encapsulates the core; wherein the subject suffers from dry eye; and wherein the administering increases production of tears in the subject. The oral dose form can be any composition disclosed herein. In some embodiments, the administering causes a statistically significant increase in tear production over baseline tear production, as measured on a Schirmer's test, for example, a 5-minute Schirmer's test. In some embodiments, after administering the oral dose form, the Schirmer's test result rises to over 5 mm, over 10 mm, over 15 mm, over 20 mm, over 25 mm, or over 30 mm of the baseline (pre-administering) Schirmer's test result. In some embodiments, after administering the oral dose form, the Schirmer's test result rises to over 125%, over 150%, over 175%, over 200%, over 250%, or over 300% of the baseline (pre-administering) Schirmer's test result. In some embodiments, administering the oral dose form causes a statistically significant reduction in tear osmolality compared to baseline. In some embodiments, after administering the oral dose form, the tear osmolality diminishes to less than 95%, less than 90%, less than 85%, less than 80%, less than 75%, or less than 70% of the baseline (pre-administering) tear osmolality. In some embodiments, administering the oral dose form causes a statistically significant improvement on a patient-reported dry eye symptom score, e.g., the Ocular Surface Disease Index. In some embodiments, after administering the oral dose form, the patient-reported score improves by a margin of at least 10%, at least 15%, at least 20%, at least 25%, at least 30%, at least 40%, or at least 50% compared to the baseline (pre-administering) patient-reported score. With any of the above methods of clinical measurement, assessment can be done after a single administration, after multiple administrations, or after chronic administration of an oral dose form or composition described herein.

The methods and compositions described herein enable a subject to orally administer the compositions to stimulate tearing, e.g., by consuming, ingesting, swallowing, chewing or sucking on a composition. In some implementations, a subject can consume a composition containing a core comprising water and allyl isothiocyanate to induce tearing. In some implementations, a subject can orally administer a composition containing a core comprising a wasabi paste hydrated with water to induce tearing. In some implementations, a subject can orally administer a composition containing a core comprising a hydrated wasabi mixture to induce tearing. A subject can orally administer a composition described herein whenever it is desirable to induce tearing, e.g., to temporarily relieve ocular pain or discomfort. The compositions can be orally administered by a subject as many times as is desirable.

The compositions disclosed herein can be self-administered by a subject based on determination by the subject that tearing is desirable, e.g., to alleviate ocular discomfort or pain. The compositions disclosed herein can be self-administered as many times as the subject believes is necessary during the course of a day, e.g., to alleviate ocular discomfort or pain. In some implementations, the compositions can be orally administered by a subject one, two, three, four, five, six, seven, eight, nine, ten, eleven, twelve or more times within 24 hours.

Methods for Treating Dry Eye

The present disclosure provides a method for treating dry eye in a subject in need thereof, the method comprising administering to the mouth of the subject an oral dose form comprising: a core comprising water and allyl isothiocyanate; and a shell, wherein the shell encapsulates the core; wherein the subject suffers from dry eye; and wherein the administering increases production of tears in the subject. The oral dose form can be any composition disclosed herein. Measurements and criteria for treating dry eye can include measurements of increased tear production (e.g., Schirmer's test), reduced tear osmolality, and/or improved patient-reported dry eye symptom scores, as described herein.

The methods and compositions disclosed herein enable a subject to orally administer the compositions to stimulate tearing to prevent or therapeutically treat and/or reduce the severity of one or more symptoms of dry eye or corneal neuropathic pain. For example, a subject experiencing the symptoms of dry eye can orally administer a composition described herein to induce therapeutic tearing, thereby reducing the severity of a dry eye symptom or preventing a dry eye symptom. In some implementations, the subject bites or chews on the composition to induce therapeutic tearing. In some implementations, the subject sucks on the composition to induce therapeutic tearing.

As used herein, "therapeutic tearing" refers to tearing that is of a sufficient amount and quality to ameliorate or reduce the severity of one or more symptoms of dry eye or corneal neuropathic pain. A reduction in the severity of one or more dry eye symptoms is noticeable to a subject and can be self-reported by a subject who has orally administered a composition as described herein to stimulate therapeutic tearing. Therapeutic tearing can also be confirmed using a diagnostic test, such as a Schirmer's test. For example, therapeutic tearing is at least an amount of tearing that will result in a normal or healthy Schirmer's test result. For example, therapeutic tearing results in at least 10 mm of moisture (wetting) or more on filter paper in 5 minutes using a Schirmer's test. In some implementations, therapeutic tearing will result in 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 30 mm, or 35 mm, e.g., 10 mm-35 mm of wetting on filter paper in 5 minutes using a Shirmer's test. Other methods for measuring tearing are also known in the art, and can be suitable for measuring therapeutic tearing, such as, but not limited to, a phenol red thread test and tear film fluorophotometry/fluorescein clearance, as described in Senchyna and Wax, *J. Ocul. Biot. Dis. Infor.* 1(1):1-6, 2008, incorporated herein in its entirety. In some implementations, tearing can be measured in the volume of tearing, and/or in the duration of tearing.

In some implementations, the subject orally administers a composition described herein to reduce one of more of the symptoms of dry eye, including, but not limited to, general ocular discomfort, a stinging, burning or scratching sensation; mucus in or around eyes; eye redness; a gritty or sandy sensation; watery eyes; blurred vision; eye fatigue; sensitivity to light; difficulty wearing contact lenses; and difficulty seeing while driving. For example, biting, chewing, or sucking on the compositions described herein induces therapeutic tearing that reduces the severity of one or more of the symptoms of dry eye, as described herein.

In some implementations, the subject orally administers the composition to alleviate symptoms of dry eye or to prevent dry eye symptoms at the subject's discretion. In some implementations, a subject orally administers a composition described herein at a time when the subject is experiencing one or more dry eye symptom. In some implementations, a subject orally administers a composition described herein at a time when the subject is not experiencing a dry eye symptom, e.g., by orally administering a composition prophylactically before the onset of a symptom of dry eye or when a subject expects the onset of a symptom of dry eye or an increase in intensity of a symptom or dry eye. In some implementations, a subject orally administers a composition described herein a certain number of times a day, or at a particular intervals of time throughout the day, so as to prophylactically prevent the onset of dry eye symptoms.

For example, a subject can orally administer a composition one or more times a day, e.g., two times a day, three times a day, four times a day, five times a day, six times a day, seven times a day, eight times a day, nine times a day, ten times a day, eleven times a day, twelve times a day, thirteen times a day, fourteen times a day, fifteen times a day, sixteen times a day, seventeen times a day, eighteen times a day, nineteen times a day, twenty times a day, twenty one times a day, twenty two times a day, twenty three times a day, twenty four times a day, or more. In some implementations, a subject orally administers a composition described herein every 15 minutes, 30 minutes, 45 minutes, 60 minutes, 1.5 hours, 2 hours, 3 hours, 4 hours, 5 hours, 6 hours, 7 hours, 8 hours, 9 hours, or 10 hours, or more.

The composition described herein can be administered in combination with one or more other processes or products that are used to treat dry eye or neuropathic corneal disease, including, for example, eye drops, artificial tears, ointments, gels, bulking agents, nutritional supplements (e.g., an omega-3 fatty acid or flaxseed oil supplements), warm compresses, medication (e.g., Shire's XIIDRA™, Allergan's RESTASIS®, topical steroids, antibiotics, such as tetracycline agents e.g., (doxycycline, azithromycin (AZA-SITE®))), products containing hypochlorus acid (e.g., AVENOVA® (Nova Bay)), punctal plugs, devices for treating meibomian gland dysfunction associated with dry eye (e.g., BLEPHEX®, LIPIFLOW®, LIPIVIEW®), and electrical neurostimulation devices that induce tearing (e.g., Allergan's TRUETEAR® (OCULEVE®) device). For example, a composition described herein can be ingested by a subject with dry eye to induce tearing, and the subject can also apply an eye drop or artificial tear that is used to treat dry eye. The co-administration of a composition disclosed herein with another process or product for treating dry eye may be carried out sequentially or simultaneously. For example, a composition containing hydrated wasabi paste can be orally administered at about the same time that another process or product for treating dry eye is administered. In another example, a composition containing hydrated wasabi paste can be orally administered before another process or product for treating dry eye has been administered. In another example, a composition containing hydrated wasabi paste can be orally administered after another process or product for treating dry eye has been administered.

EXAMPLES

The invention is further described in the following examples, which do not limit the scope of the invention described in the claims.

Example 1

Encapsulation

Wasabi paste was encapsulated using various methods to determine whether wasabi paste can be prepared into discreet ingestible compositions (e.g., capsules, candies or lozenges) that can be stored until later ingestion, while retaining the pungency necessary to induce tearing effectively.

Powder produced from wasabi plants (purchased from World of Wasabi), or powder produced from horseradish, was mixed with water to produce a hydrated paste, following the instructions provided by the producers of the respective powders. Cold water was added to wasabi powder or horseradish powder at a ratio of 1:1 to 5:3 (powder to water), and allowed to sit for 5 to 15 minutes. The resulting paste was divided into individual doses that each contained a "pea-sized" amount of the paste. These individual doses were used to make the cores of the individual units of the ingestible compositions. Preferably, the cores are encapsulated shortly after water is added to the wasabi or horseradish powder, because the pungency of the hydrated wasabi or hydrated horseradish begins to fade at about 15 minutes after water is added. The cores were encapsulated in one of three different types of shells. First, some cores were each placed in a commercially-purchased hypromellose capsule (Capsugel). Second, some cores were encapsulated in a hard candy outer coating made from a melted mixture of water (one part), sugar (two parts), and corn syrup (0.5 part). Third, some cores were placed in the hypromellose capsule and then coated with a hard candy outer coating (one-part water, two parts sugar, 0.5-part corn syrup).

Example 2

Assessment of Tear Stimulation by Encapsulated Wasabi Paste

Compositions produced as described in Example 1 were tested for their ability to stimulate tearing after ingestion by a subject. The presence or absence of tearing was registered after a subject separately ingested each of the following types of compositions: (1) hydrated wasabi paste encapsulated in a hypromellose capsule; (2) hydrated wasabi paste encapsulated in a hard candy coating; (3) hydrated wasabi paste encapsulated in a hypromellose capsule and a hard candy coating; (4) hydrated horseradish paste encapsulated in a hypromellose capsule; (5) hydrated horseradish paste encapsulated in a hard candy coating; (6) hydrated horseradish paste encapsulated in a hypromellose capsule and a hard candy coating. The subject waited a period of time after orally administering each of the compositions so as to allow recovery from tearing or other physical manifestations caused by consuming the composition, before ingesting a different composition. Each of the three wasabi paste preparations induced tearing in the subject.

Each of the compositions prepared from wasabi were tested for their ability to induce tearing after storage for one week at room temperature. All three of the wasabi paste preparations induced tearing after ingestion following one week of storage at room temperature or one week of storage in a refrigerator, showing that each of the encapsulation methods could maintain the pungency of the hydrated wasabi paste after extended storage under different conditions.

Example 3

Clinical Testing of Tear Stimulation

A clinical trial is conducted to understand the degree to which compositions prepared from wasabi can induce tearing, and how consistently the compositions can induce tearing among different subjects. Compositions containing different amounts of wasabi or different preparations of wasabi paste are tested and compared for their ability to induce tearing. For example, compositions containing wasabi paste having different water content levels are compared. The amounts of wasabi paste necessary to induce reflex consistently among subjects are tested for each wasabi paste preparation. The clinical trial is also used to understand the amount of variation between subjects in their sensitivity to the wasabi compositions.

A clinical trial is also used to confirm the levels of tearing produced to therapeutically alleviate symptoms of dry eye, and the length of time such symptoms are relieved following ingestion of a wasabi composition. Subjects having dry eye disease consume wasabi compositions, as prepared in Example 1, when dry eye symptoms are present. The dry eye subjects are monitored using an eye examination to determine to what extent the composition has reduced a symptom of dry eye, and by asking the subjects about the severity of their symptoms. Changes in tearing following oral administration of the composition by dry eye subjects are also monitored using the Schirmir's test. The effects are compared to the effects in subjects without dry eye disease.

Example 4

Assessment of Storage Conditions on Efficacy

A series of tests are conducted to determine the effects of storage time, storage temperature, and packaging on the efficacy of wasabi-based compositions to induce tearing. The tests determine the length of time the different preparations of wasabi-based compositions can be stored at different temperatures in different types of packaging, while retaining pungency and the capability to induce tearing.

Compositions containing different preparations of wasabi paste (e.g., wasabi paste with different levels of water content) encapsulated in hypromellose, a hard candy coating, or hypromellose and a hard candy coating, are stored at different temperatures for different lengths of time before being orally ingested. For example, the different compositions are stored at room temperature (e.g., between 60° F. to 75° F.), and at higher and lower temperatures (e.g., between 0° F. to 95° F., 0° F. to 4° F., 0° F. to 32° F., 32° F. to 59° F., or 76° F. to 80° F.) for 2 weeks, 4 weeks, 6 weeks, 8 weeks, 12 weeks, 16 weeks, 32 weeks and up to a year, and then tested for the capability to induce tearing. The compositions are stored in different packaging, e.g., blister packs or bottles, and compared to compositions that have been stored under the same conditions without packaging. The compositions will be ingested in parallel with wasabi compositions that have been newly produced to assess potential loss in tear-inducing capability due to the different storage conditions.

Example 5

Comparison of Dry Wasabi and Hydrated Wasabi

A crossover study was conducted on four human volunteers to compare the effects of dry wasabi and hydrated wasabi, when orally administered to the volunteers, on tear production as measured by the Schirmer's test. A Schirmer's test was conducted on each volunteer to test baseline tear production. Volunteers were then randomly assigned to receive dry wasabi powder or a hydrated wasabi paste (containing an equivalent amount of dry wasabi powder) by mouth, and then the wasabi powder or paste was administered. Concurrently, another Schirmer's test was run for 5 minutes to test changes in tear production as a result of receiving the wasabi powder or paste. Upon completion of that test, volunteers waited at least another 5 minutes. Next, the volunteer received the comparator material (i.e., volunteers who previously took dry wasabi powder took the hydrated wasabi paste, and vice-versa). Concurrently, another Schirmer's test was run for 5 minutes.

The results of this study showed that the mean baseline Schirmer's value was 7.1 mm. Dry wasabi caused a mean 4 mm increase in the Schirmer's value, which was not statistically significant (p=0.24 by paired t-test). All volunteers showed brisk increases in tear production, versus baseline, in response to the wet wasabi. Wet wasabi caused a mean 17.1 mm increase in the Schirmer's value (p<0.001 vs. baseline; p=0.015 versus dry wasabi; each by paired t-test).

In conclusion, a controlled crossover study showed that wet wasabi, when orally administered to human volunteers, caused a significant increase in tear production. Oral administration of an equivalent amount of dry wasabi did not significantly increase tear production.

Example 6

Clinical Trial

A prospective placebo-controlled, investigator-masked clinical trial was conducted on six patients affected by dry eye disease to test the effects of orally administered, hydrated wasabi paste on tear production. The individual performing the Schirmer's tests did not know whether the patient had received wasabi paste or placebo. A Schirmer's test was conducted on each patient to record baseline tear reduction. Patients were then randomly assigned to receive a pea-sized dose of wet wasabi paste or placebo (watermelon toothpaste) by mouth, and were administered the the wasabi paste or control. Concurrently, another Schirmer's test was run for 5 minutes to test changes in tear production as a result of the wasabi or placebo.

The results of this study showed that the mean baseline Schirmer's value was 5.3 mm. Placebo was associated with a mean 0.75 mm reduction in the Schirmer's value, which was not statistically significant (p=0.58 by paired t-test). Patients who received wet wasabi paste, on the other hand, showed brisk increases in tear production versus baseline. Wet wasabi caused a mean 24.2 mm increase in the Schirmer's value (p<0.05 vs. baseline; p<0.05 versus placebo; each by paired t-test).

In conclusion, a prospective, placebo-controlled, investigator-masked clinical trial showed that wet wasabi, when orally administered to patients with dry eye disease, caused a significant increase in tear production. Oral administration of placebo did not increase tear production.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating dry eye disease in a subject, the method comprising identifying a subject with dry eye and administering to the mouth of the subject an oral dose form comprising an effective amount of allyl isothiocyanate for stimulating tearing and hypromellose, wherein the effective amount of allyl isothiocyanate is between 0.0001 to about 5% by weight of the oral dose form, and wherein administering the oral dose form increases production of tears in the subject by over 10 mm, as measured on a Schirmer's test.

2. The method of claim 1, wherein the oral dose form comprises a core comprising the allyl isothiocyanate.

3. The method of claim 2, wherein the core further comprises water.

4. The method of claim 3, wherein the core comprises hydrated wasabi paste.

5. The method of claim 2, wherein the oral dose form further comprises a shell.

6. The method of claim 5, wherein the shell comprises the hypromellose.

7. The method of claim 1, wherein the allyl isothiocyanate is derived from hydrated wasabi paste.

8. The method of claim 1, wherein administering the oral dose form increases tear production by over 15 mm, as measured on a Schirmer's test.

9. The method of claim 1, wherein administering the oral dose form increases tear production by over 20 mm, as measured on a Schirmer's test.

* * * * *